(12) United States Patent
Davis et al.

(10) Patent No.: US 8,038,657 B2
(45) Date of Patent: Oct. 18, 2011

(54) SYSTEMS AND METHODS FOR PROVIDING AN IV ADMINISTRATION SET INCORPORATING DRIP MONITORING CIRCUITRY

(75) Inventors: Bryan G. Davis, Sandy, UT (US); Austin Jason McKinnon, Herriman, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 83 days.

(21) Appl. No.: 12/503,678

(22) Filed: Jul. 15, 2009

(65) Prior Publication Data

US 2011/0015583 A1  Jan. 20, 2011

(51) Int. Cl.
*A61M 5/14* (2006.01)

(52) U.S. Cl. ........................................................ 604/253

(58) Field of Classification Search .................. 604/251, 604/253, 255
See application file for complete search history.

(56) References Cited

U.S. PATENT DOCUMENTS 4,583,975 A * 4/1986 Pekkarinen et al. .......... 604/253
* cited by examiner

*Primary Examiner* — Theodore Stigell
*Assistant Examiner* — Deanna K Hall
(74) *Attorney, Agent, or Firm* — Mony R. Ghose; Kirton & McConkie

(57) ABSTRACT

A circuitry for counting drips and monitoring a rate of infusion is incorporated into an IV administration set. The circuitry includes a pair of leads that are positioned in the pathway of fluid droplets, such that each droplet simultaneously contacts both leads. As such, the leads act as a virtual switch that is closed by the presence of a droplet. This event is then displayed on a drip signaling device to aid a user in adjusting the infusion rate of the IV administration set.

20 Claims, 15 Drawing Sheets

SYSTEMS AND METHODS FOR PROVIDING AN IV ADMINISTRATION SET INCORPORATING DRIP MONITORING CIRCUITRY

BACKGROUND OF THE INVENTION

The present invention relates to systems and methods for providing an IV administration set equipped with a drip chamber having flow monitoring capabilities. Specifically, the present invention provides an IV administration set incorporating leads that are positioned in the flow pathway of the system. The leads are part of an electrical circuit that is closed and opened by the presence of fluid in the form of drops.

An IV administration set is commonly used to deliver to or retrieve from a patient a fluid, such as blood, a medicament, a nutritional supplement, or a solution. IV administration sets generally include a coupling assembly having a first end configured to access a fluid reservoir and having a second end equipped with a conduit for insertion into a patient. The coupling assembly further includes a drip chamber into which fluid from the fluid reservoir is collected prior to infusion into the patient via the conduit.

The rate at which a fluid flows through the IV administration set must be carefully monitored to ensure that the fluid is being infused in a proper and safe manner. The infusion rate is determined based on the number of drips that enter the drip chamber over a certain period of time. One method of controlling the infusion rate is to use an inline, electronically controlled pump to monitor the flow through the IV set. This type of pump typically includes a logic that permits a user to indicate a desired flow which in turn adjusts the speed of the pump. While these pumps are effective and useful, they require a power source that may not be available.

Another method of controlling the infusion rate is to use a clamp to partially occlude the flow through the conduit. A roller clamp, or similar clamping device, is commonly used to selectively occlude the conduit of the IV administration set thereby controlling the rate at which the fluid flows though the system. This typically requires a user to set the clamp and then count the drops as they enter the drip chamber. Depending upon how many drops are counted over a period of time, the user may be required to adjust the degree of occlusion until the desired infusion rate is achieved. This latter method, while effective, is not entirely accurate or convenient. For example, roller clamps are known to drift causing variation in the flow rate in the system.

Thus, while methods currently exist for setting an infusion rate for an IV administration set, challenges still exist. Accordingly, there is a need in the art for an IV administration set having flow monitoring capabilities, which provides means for dealing with the drawbacks of currently available methods. Such an IV administration set is disclosed hererin.

BRIEF SUMMARY OF THE INVENTION

The present invention relates to systems and methods for providing an IV administration set having flow monitoring capabilities. Specifically, the present invention provides an IV administration set incorporating leads that are positioned in the flow pathway of the system. The leads are part of an electrical circuit that is closed and opened by the presence of fluid in the form of drops. The leads may include any material, or coating material, that is electrically conductive.

The leads are generally attached to a coupling assembly of the IV set at a position proximal to the fluid pathway of the system. In some embodiments, the leads extend inwardly from the coupling assembly and into a drip chamber of the IV set. As such, the exiting droplets of fluid simultaneously contact the leads which act as a virtual switch for the circuit. In other embodiments the leads are deposited on an outer surface of the coupling assembly proximate to the output of the coupling assembly. Still, in other embodiments a central lead is positioned in a fluid channel of the coupling assembly, and a second, external lead is positioned on an outer surface of the coupling assembly proximate to the fluid outlet of the coupling assembly.

The IV set of the current invention is further used in conjunction with a signaling device, or other device configured to indicate or record droplets of fluid through the IV set. For example, the signaling device may include a light bulb, a light emitting diode, a speaker, a digital display readout, or combination thereof. In some embodiments, the coupling assembly further includes an external terminal contact electrically coupled to each lead, whereby the signaling device is coupled to the lead via the terminal contact. In other embodiments, the signaling device is integrated into the coupling assembly and is therefore disposable following use.

In some embodiments a reusable signaling device is configured to reversibly couple to an outer surface of the coupling assembly during administration with the IV set. Following use of the IV set, the signaling device is removed and the remainder of the IV set is discarded. Still, in other embodiments a signaling device is configured with extension leads that are configured to attach to the terminal contacts. The invention further includes methods for processing signal data from the circuit to enable accurate drip detection.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof which are illustrated in the appended drawings. These drawings depict only typical embodiments of the invention and are not therefore to be considered to limit the scope of the invention.

DETAILED DESCRIPTION OF THE INVENTION

The presently preferred embodiments of the present invention will be best understood by reference to the drawings, wherein like reference numbers indicate identical or functionally similar elements. It will be readily understood that the components of the present invention, as generally described and illustrated in the figures herein, could be arranged and designed in a wide variety of different configurations. Thus, the following more detailed description, as represented in the figures, is not intended to limit the scope of the invention as claimed, but is merely representative of presently preferred embodiments of the invention.

Figure 1A:
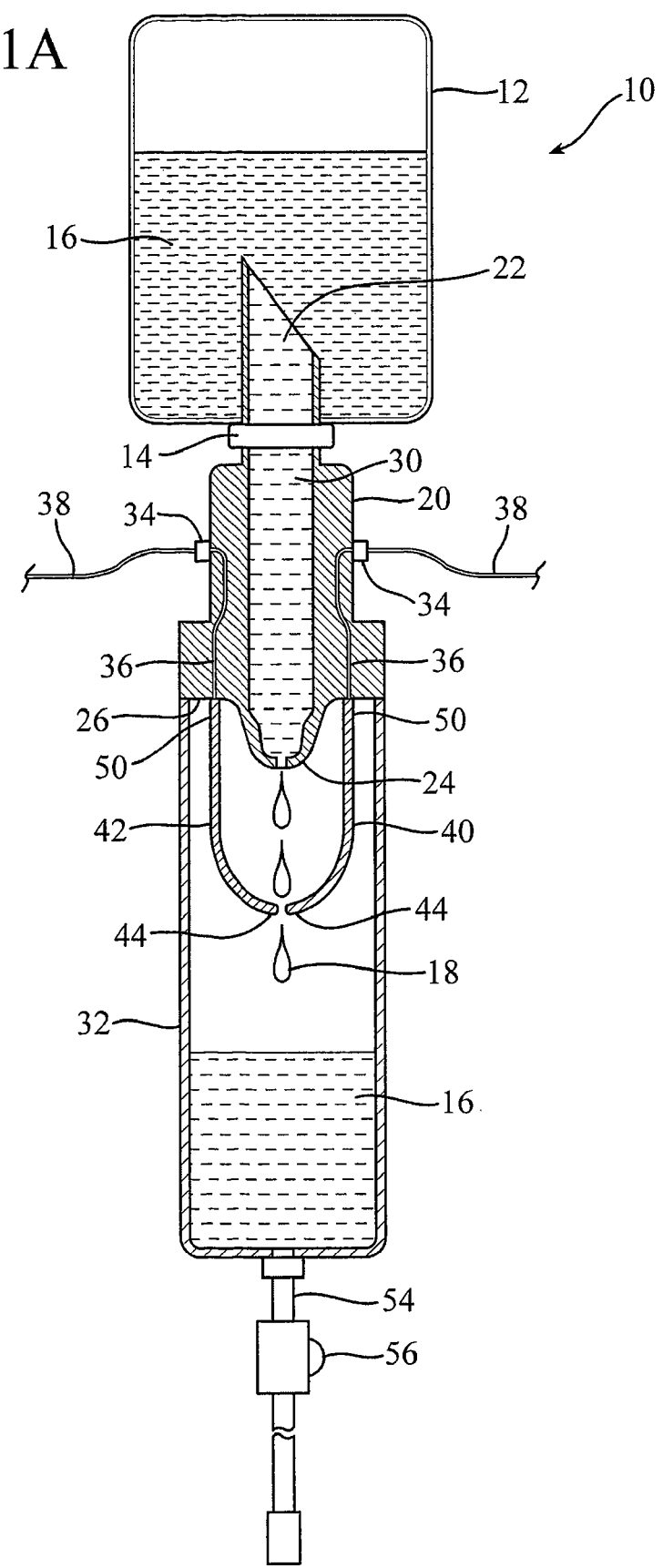
FIG. 1A is a cross-sectioned view of an implementation of an IV administration set having a set of drip detecting leads.

Referring now to FIG. 1A, a cross section of an implementation of an IV administration set 10 is shown. The IV administration set 10 generally includes a coupling assembly 20 having an input 22 and an output 24. The coupling assembly 20 is fluidly coupled to a drip chamber 32 configured to receive and hold fluid 16 from the fluid reservoir 12. The IV set 10 further includes a fluid channel 30 by which the input 22 and the output 24 are fluidly connected. The input 22 is configured to insert within the fluid reservoir 12. The fluid reservoir 12 generally comprises an IV bag or bottle containing a fluid, such as a medicament, a solution, or a nutritional supplement intended for administration to a patient via the IV administration set 10. The fluid reservoir 12 further includes a seal or septum 14 that is punctured or otherwise accessible by the input 22 to establish fluid communication between a fluid 16 within the fluid reservoir 12 and the fluid channel 30.

The fluid 16 flows from the fluid reservoir 12 through the coupling assembly 20 via the fluid channel 30. The fluid 16 exits the coupling assembly 20 into the drip chamber 32 via the output 24. The fluid generally pools in the drip chamber 32 and eventually exits the drip chamber 32 via a patient conduit 54. The patient conduit 54 comprises a section of intravenous tubing that is attached to the venous system of a patient via a needle (not shown). In some embodiments, the patient conduit 54 further includes an adjustable clamp 56, such as a roller clamp, that permits the user to selectively occlude the conduit 54 thereby limiting the flow of the fluid 16 through the conduit 54.

In some embodiments, the output 24 of the coupling assembly 20 is configured to direct or guide the exiting fluid 18 towards a first and a second lead 40 and 42 of the coupling assembly 20. The first and second leads 40 and 42 are fixedly attached to the distal end 26 of the coupling assembly 20, and extend downwardly into the drip chamber 32. In some embodiments, terminal ends 50 of the first and second leads 40 and 42 are molded into the coupling assembly 20 such that the leads 40 and 42 become an integral part of the coupling assembly 20. In other embodiments, the terminal ends 50 of the first and second leads 40 and 42 are attached to the distal end 26 of the coupling assembly 20 via an epoxy, glue, or an adhesive strip.

In some embodiments of the present invention, the coupling assembly 20 further comprises a contact pad or terminal 34. The terminal 34 is located on an outer surface of the coupling assembly 20 so as to be externally accessible during use of the IV administration set 10. The terminal 34 may include any electrically conductive material, such as a metallic material including wire, foil, mesh, and tape. In some embodiments the terminal 34 extends outwardly beyond the outer surface of the coupling assembly 20. In other embodiments, the outer surface of the terminal 34 is flush with the outer surface of the coupling assembly 20. The terminal 34 is electrically coupled to the terminal ends 50 of the first and second leads 40 and 42 via a lead wire 36. The lead wire 36 is coupled to both the terminal end 50 of the leads 40 and 42 as well as to a portion of the terminals 34. In some embodiments, the lead wire 36 is routed internally through a portion of the coupling assembly 20 extending from the terminal 34 to the leads 40 and 42. In other embodiments, the lead wire 36 is routed externally over the outer surface of the coupling assembly 20 to span the distance between the terminals 34 and the respective leads 40 and 42, as shown and discussed in FIGS. 4 and 8 below.

The leads 40 and 42 may comprise any electrically conductive material, such as a metallic material including wire, foil, mesh, and tape. In some embodiments, the leads 40 and 42 comprises a non-electrically conductive material, yet further comprise an electrically conductive coating material, such as a polymer, an epoxy, a paint, a grease, a sealant, an elastomer, or a carbon coating. In other embodiments, the leads 40 and 42 comprise a non-electrically conductive extension of the coupling assembly 20 material, and a portion of the leads 40 and 42 are coated with an electrically conductive material.

For each embodiment, contact portions 44 of the first and second leads 40 and 42 are positioned in the pathway of the exiting fluid 18. As such, the exiting fluid 18 simultaneously contacts the respective contact portions 44 of the first and second leads 40 and 42. In some embodiments, this simultaneous contact of the first and second leads 40 and 42 completes a circuit, as shown in FIG. 1B.

Figure 1B:
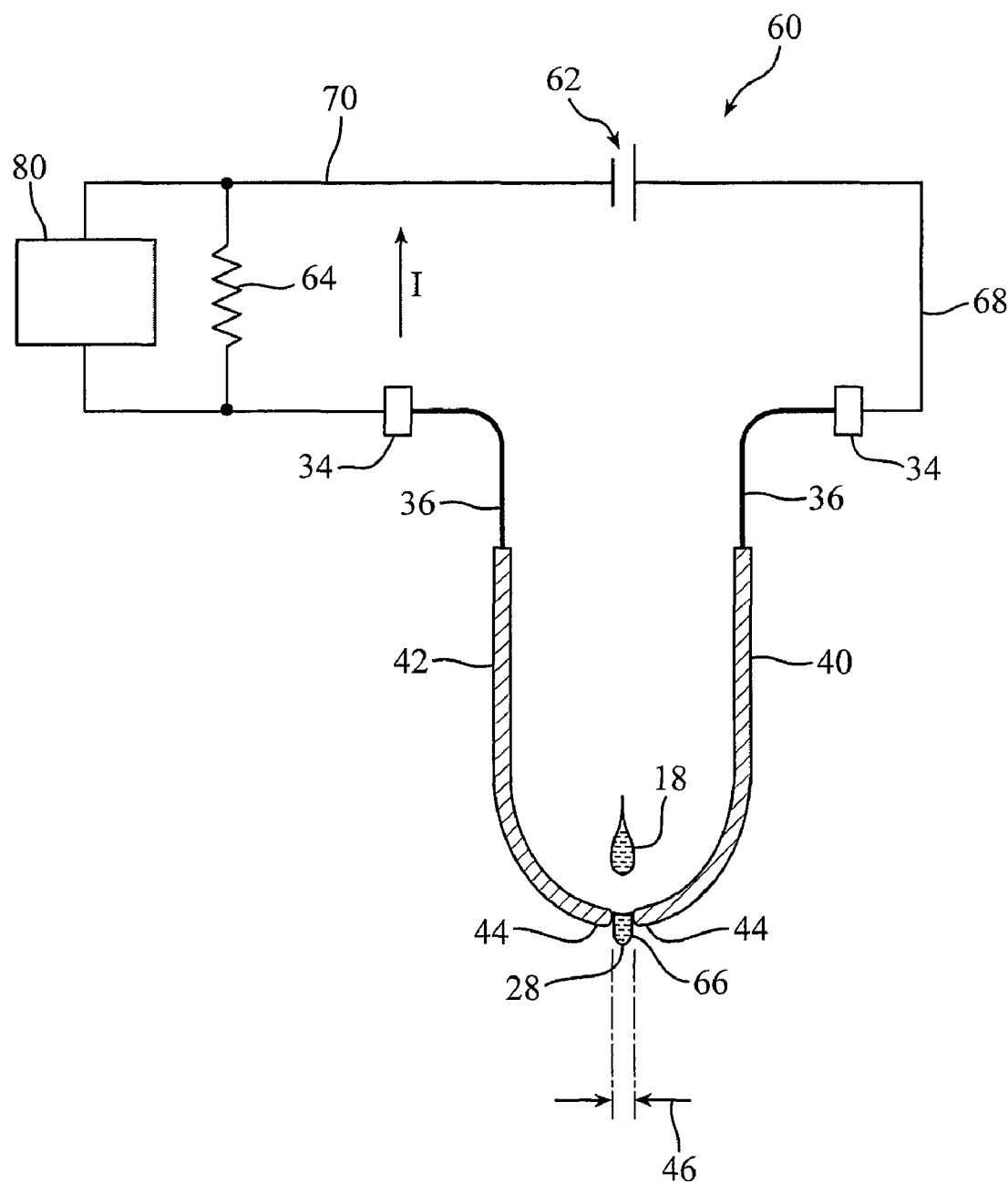
FIG. 1B is a schematic of a circuit in accordance with the present invention.
Figure 2A:
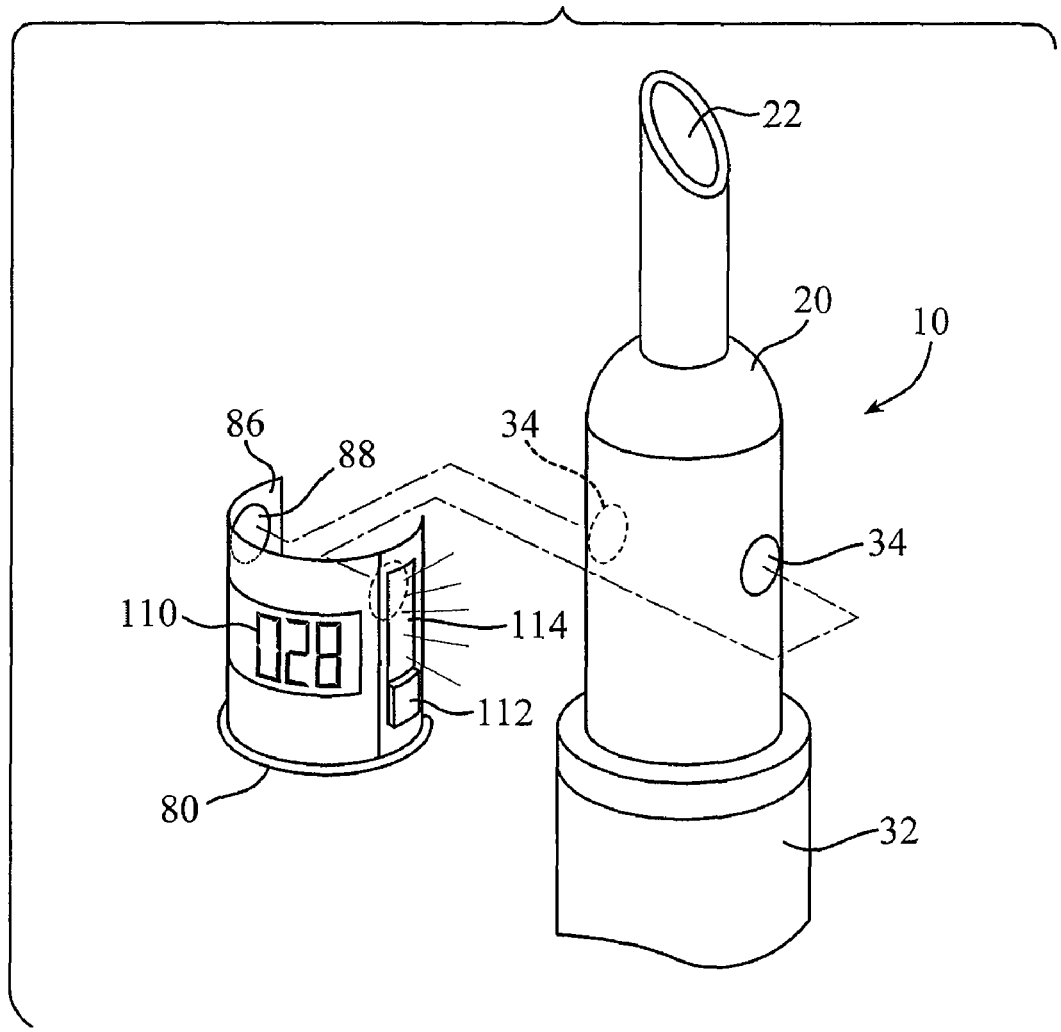
FIG. 2A is an exploded perspective view of a signaling device and a coupling assembly of an IV administration set.
Figure 2B:
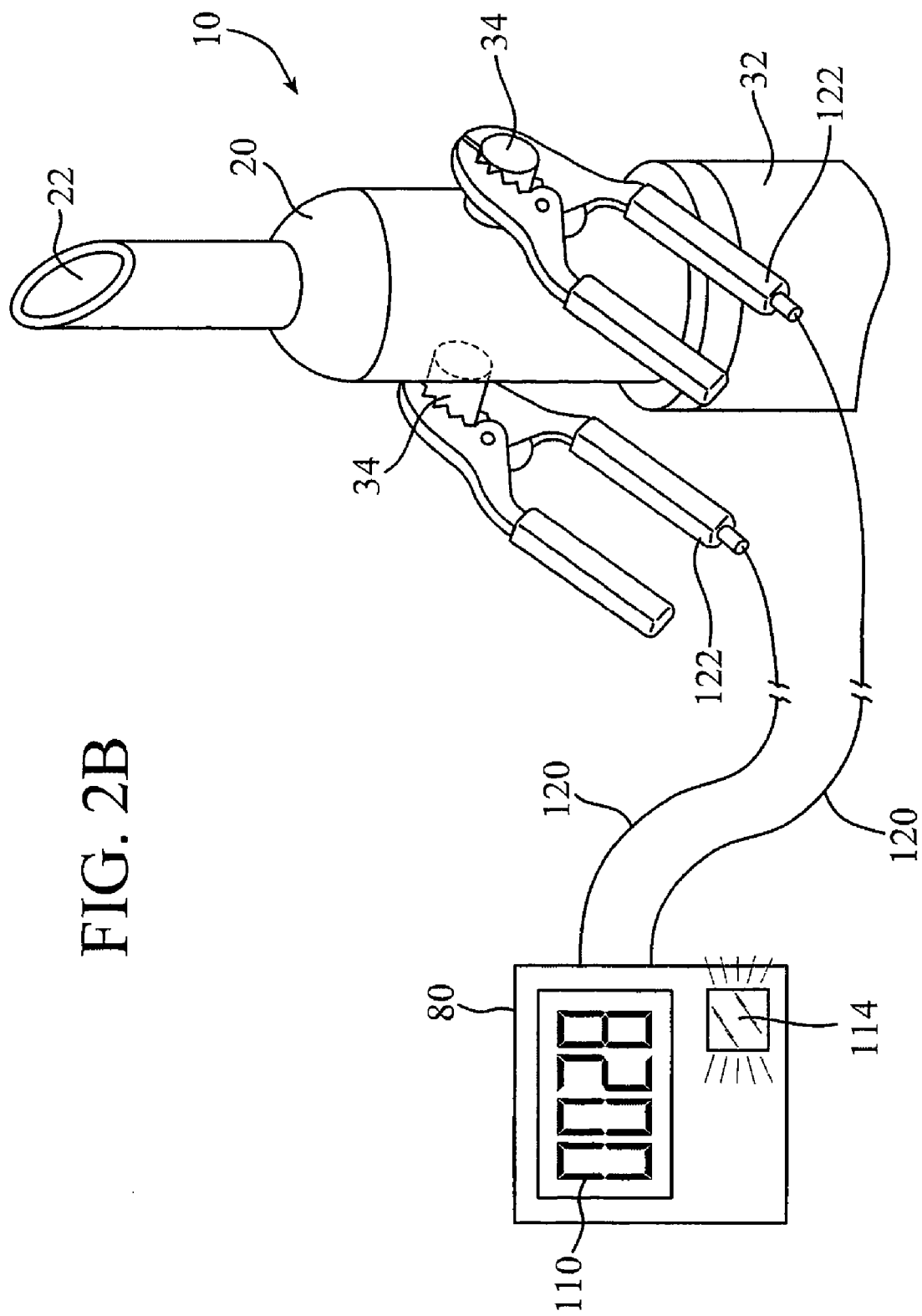
FIG. 2B is a perspective view of a signaling device coupled to an IV administration set via a pair of extension leads.
Figure 2C:
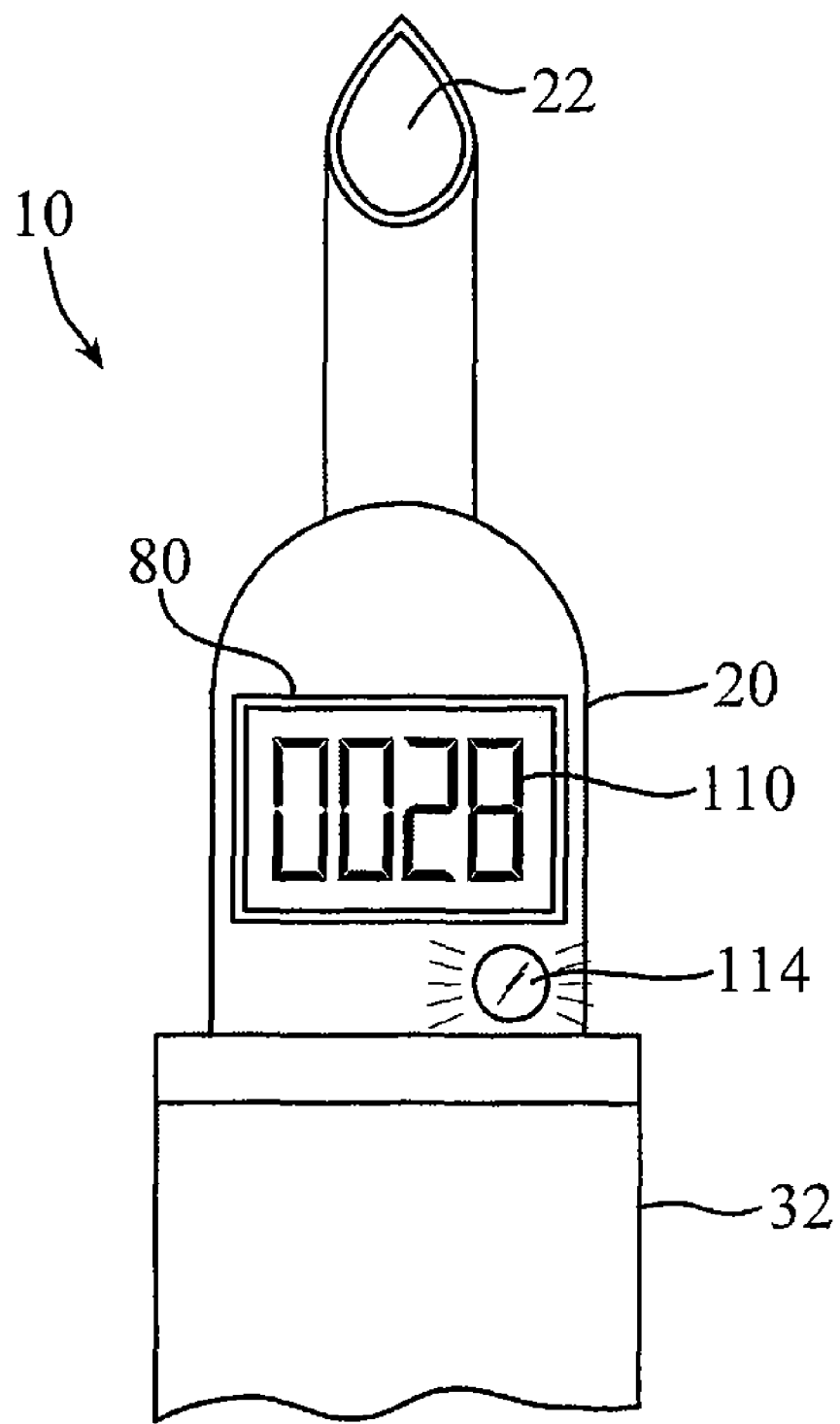
FIG. 2C is a perspective view of a coupling assembly having a signaling device incorporated therein.

Referring now to FIG. 1B, a circuit 60 is shown. In some embodiments of the present invention, the IV administration set 10 further comprises a circuit 60 to sense the fluid droplets 18 as they fall. In some embodiments the circuit 60 resides in an external signaling device, as shown in FIGS. 2A-2C, below. In other embodiments, the circuit 60 is incorporated into the coupling assembly 20 of the IV set 10. The circuit 60 generally includes a voltage supply 62, such as a small battery, having a positive line 68 connected to the first lead 40, and a negative line 70 connected to the second lead 42. The circuit 60 further includes electrical current detector such as a first resistor 64 interposedly connected to the negative line 70 between the voltage supply 62 and the second lead 42. A space or gap 46 is further provided between the contact portions 44 of the first and second leads 40 and 42. The gap 46 provides a break in the circuit 60. The gap 46 therefore acts as a virtual switch that is closed when a drop 18 of fluid simultaneously contacts the contact portions 44 of the first and second leads 40 and 42. When a droplet 18 thus becomes engaged, the engaged droplet 28 closes the circuit 60, as shown.

In addition to closing the circuit 60, the engaged droplet 28 also acts as a second resistor 66 to decrease the current through the circuit 60. Additionally, the combined resistance of the first and second resistors 64 and 66 may decrease electrical current of the circuit 60 to prevent ionization of the passing droplets 18. In some embodiments, the capacity of the first resistor 64 ($R_1$) is selected to be approximately equal to the capacity of the second resistor 66 ($R_2$). As such, the detectable voltage ($V_{out}$) across the first resistor 64 is approximately equal to one-half of the voltage supply 62 ($V_{supply}$), according to Ohm's law, as shown in Equation 1.

$$V_{out}/V_{supply} = R_1/(R_2+R_1) \qquad \text{Equation 1}$$

For example, in one embodiment the voltage supply 62 is equal to 3V, and the second resistor 66 has a capacity of 1 MΩ. Thus, if the second resistor 66 is set to 1 MΩ, then the drop in voltage across the second resistor 66 is equal to one-half the voltage supply 62, or approximately 1.5V. Also, by Ohm's law, the current through the system of this example is about 1.5μ Ampers. Therefore, the circuit 60 provides a convenient method for monitoring droplets 18 through the system 10 based on predicted changes in voltage, as explained.

In some embodiments, the circuit 60 further includes a voltage signaling device 80, or other device for detecting changes in the voltage or current of the circuit 60. In some embodiments, the first resistor 64 is interposedly positioned between the signaling device 80 and the remainder of the circuit 60, such that the signaling device 80 measures voltage drop across the first resistor 64. As such, the signaling device 80 measures the drop in voltage or current across the first resistor 64. In other embodiments, the first resistor 64 is integrated into the signaling device 80. The signaling device may include any device capable of measuring, or otherwise detecting a voltage or amperage change with the circuit. For example, in some embodiments the signaling device 80 is a light bulb, and the first resistor 64 is the filament of the light bulb. In other embodiments, the signaling device 80 is a light emitting diode. Still in other embodiments, the signaling device 80 is a digital readout display or a digital counter. In other embodiments, the signaling device 80 is a speaker or other device configured to provide an audible signal indicating a change in the voltage of the circuit 60.

Referring again to FIG. 1A, the contact terminals 34 may include external lead wires 38 which may be coupled to an external signaling device 80. Alternatively, the contact terminals 34 may be configured to compatibly interact with a set of contacts on an external signaling device 80, as shown in FIG. 2A.

Referring now to FIG. 2A, an exploded view of a coupling assembly 20 and an external signaling device 80 is shown. In this embodiment, the signaling device 80 comprises a digital display 110 and a chipset 112 having logic to facilitate drip counting and recording on the display 110. In some embodiments, the signaling device 80 further comprises a signal light 114 to provide a visual indication for drip counting. Alternative embodiments may also include a speaker or other device to provide an audible alert.

In some implementations of the present invention, the signaling device 80 comprises a partial sleeve configuration having an inner surface 86 that is contoured to mirror an outer surface of the coupling assembly 20. As such, the inner surface 86 of the signaling device 80 compatibly couples to the external surface of the coupling assembly 20. Additionally, the interior surface 86 of the signaling device 80 comprises a pair of contacts 88 that are position to align with the terminal contacts 34 of the coupling assembly 20 during coupling of the signaling device 80 and the coupling assembly 20. In some embodiments, the coupling assembly 20 further comprises a catch (not shown) to compatibly receive a ridge (not shown) or other feature of the signaling device 80 to maintain the coupled positions of the signaling device 80 and the coupling assembly 20. In other embodiments, the inner surface 86 of the signaling device 80 is inwardly biased such that the inner surface 86 pinches, or otherwise clamps onto the outer surface of the coupling assembly 20 in a reversible manner. Finally, in another embodiment the inner surface 86 of the signaling device 80 comprises channels (not shown) adapted to receive an outwardly extended surface of the terminal contacts 34. As such, the signaling device 80 is coupled to the coupling assembly 20 by aligning the channels (not shown) with the terminal contacts 34 and engaging the two components such that the contacts 88 and the terminal contacts 34 are connected. One of skill in the art will appreciate that many methods can be used to interconnect the signaling device 80 and the coupling assembly 20 in accordance with the spirit of the present invention.

Referring now to FIG. 2B, an implementation of an embodiment of the present invention is shown having outwardly extended terminal contacts 34. As shown, in some embodiments the terminal contacts 34 are extended outwardly so as to provide a positive surface by which to attach a signaling device 80. In some embodiments, the signaling device 80 further includes extension leads 120 and clips 122 to facilitate coupling of the signaling device 80 to the terminal contacts 34 of the coupling assembly 20. As such, the signaling device 80 may be located separately from the remainder of the IV administration set 10.

Referring now to FIG. 2C, an implementation of an embodiment of the present invention is shown having an integrated signaling device 80 and display 110. In some embodiments, the outer surface of the coupling assembly 20 is modified to include a drip signaling device 80 display 110. In these embodiments, the display 110 is internally connected to the first and second leads 40 and 42 (not shown) thereby eliminating the need for terminal contacts. In other embodiments, the coupling assembly 20 is modified to include a signal light 114 to provide a visual indicator of drips passing though the IV administration set 10.

Figure 3A:
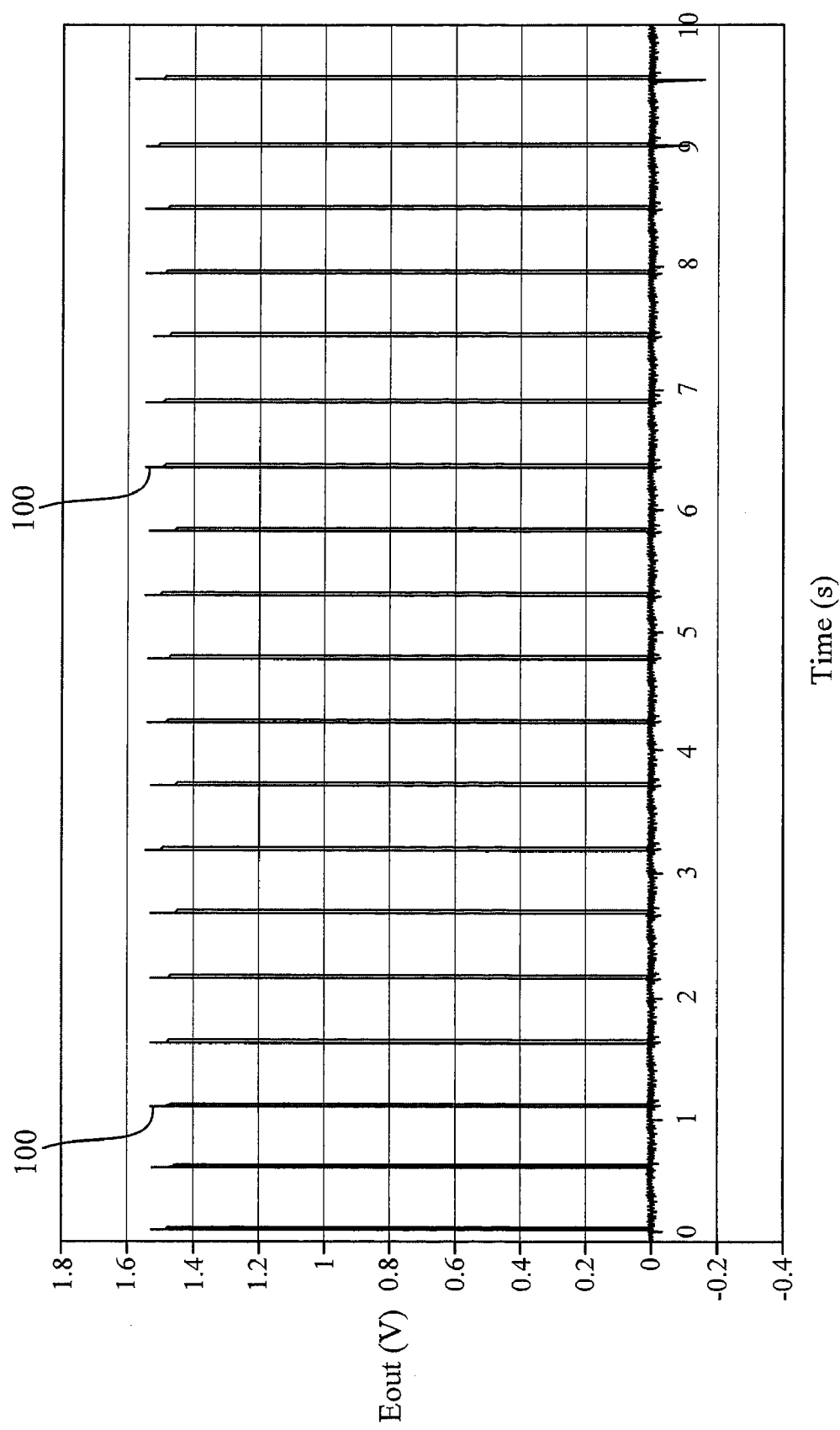
FIG. 3A is a graph displaying results from a slow drip through the IV administration set of FIG. 1A.

Referring now to FIGS. 3A-3D, various graphs are shown displaying signal patterns obtained from the use of IV administration sets 10 equipped with a drip monitoring device, as previously discussed. The objective of all drip counter signal processing is that one trigger event 90 occurs for each drip 18 that falls. Referring now to FIG. 3A, a voltage signal pattern is shown from a slow drip through an embodiment as shown in FIG. 1. In FIG. 3A, $V_{out}$ was sampled at 1000 Hz. As such, each of the seemingly narrow peaks 100 is actually comprised of many data points. Thus, a simple voltage threshold trigger would trigger many times for each drip, and would therefore not be adequate. Therefore, a clean signal such as the one shown in FIG. 3A, can most easily be processed by using a slope triggering algorithm, as demonstrated in FIG. 3B.

Figure 3B:
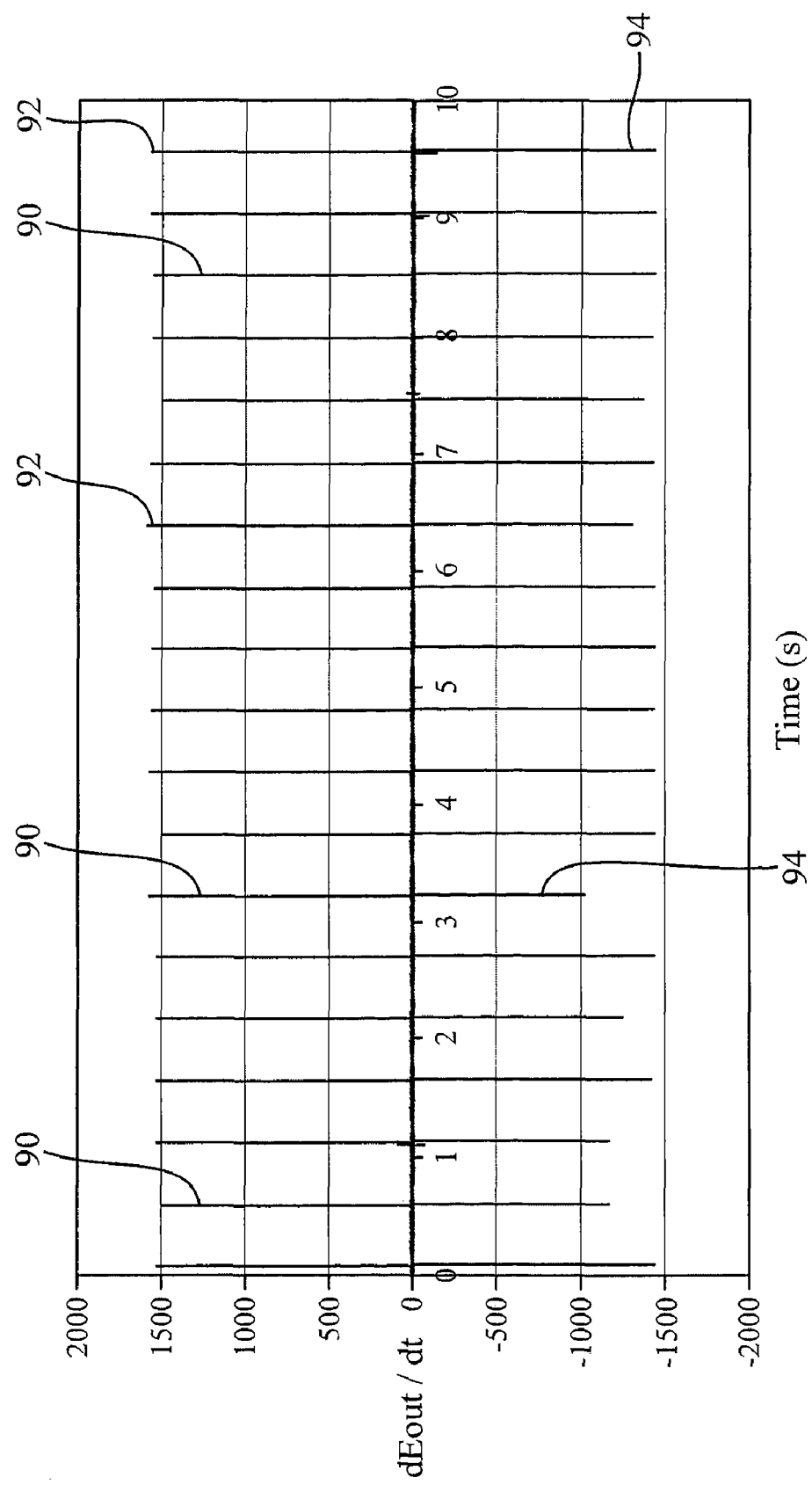
FIG. 3B is a graph displaying the time derivative of the graph in FIG. 3A.

Referring now to FIG. 3B, the time derivative of the voltage signal of FIG. 3A is shown. The positive spikes 92 indicate when the circuit 60 was closed by the drip 18, and the negative spikes 94 indicate when the circuit 60 was again reopened by the drip 18 leaving the contact portions 44 of the first and second leads 40 and 42. In this case, the slope threshold can be set at about 1000 V/sec. which will result in a single trigger event 90 per drip 18.

Figure 3C:
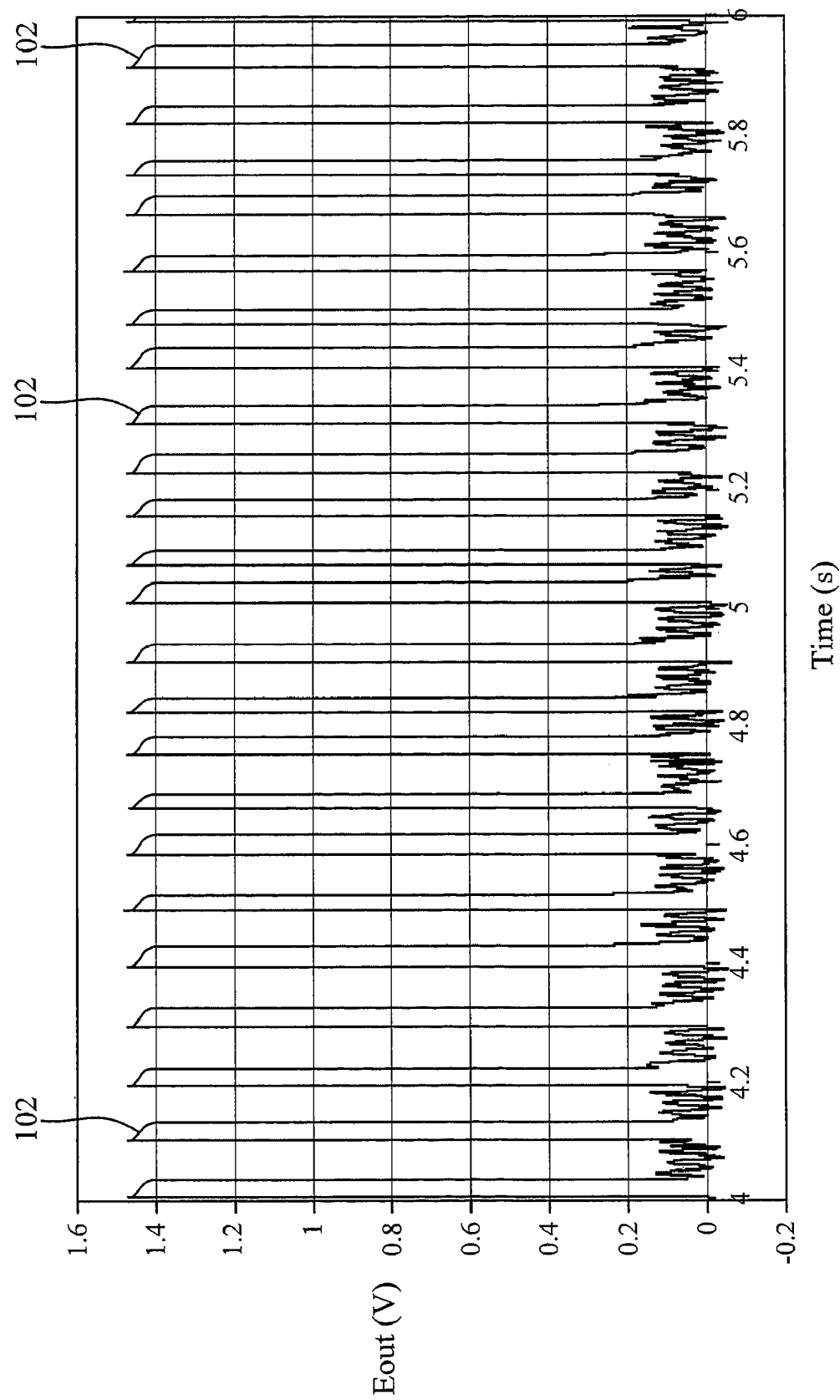
FIG. 3C is a graph displaying results from a fast drip through the IV administration set of FIG. 1A.
Figure 3D:
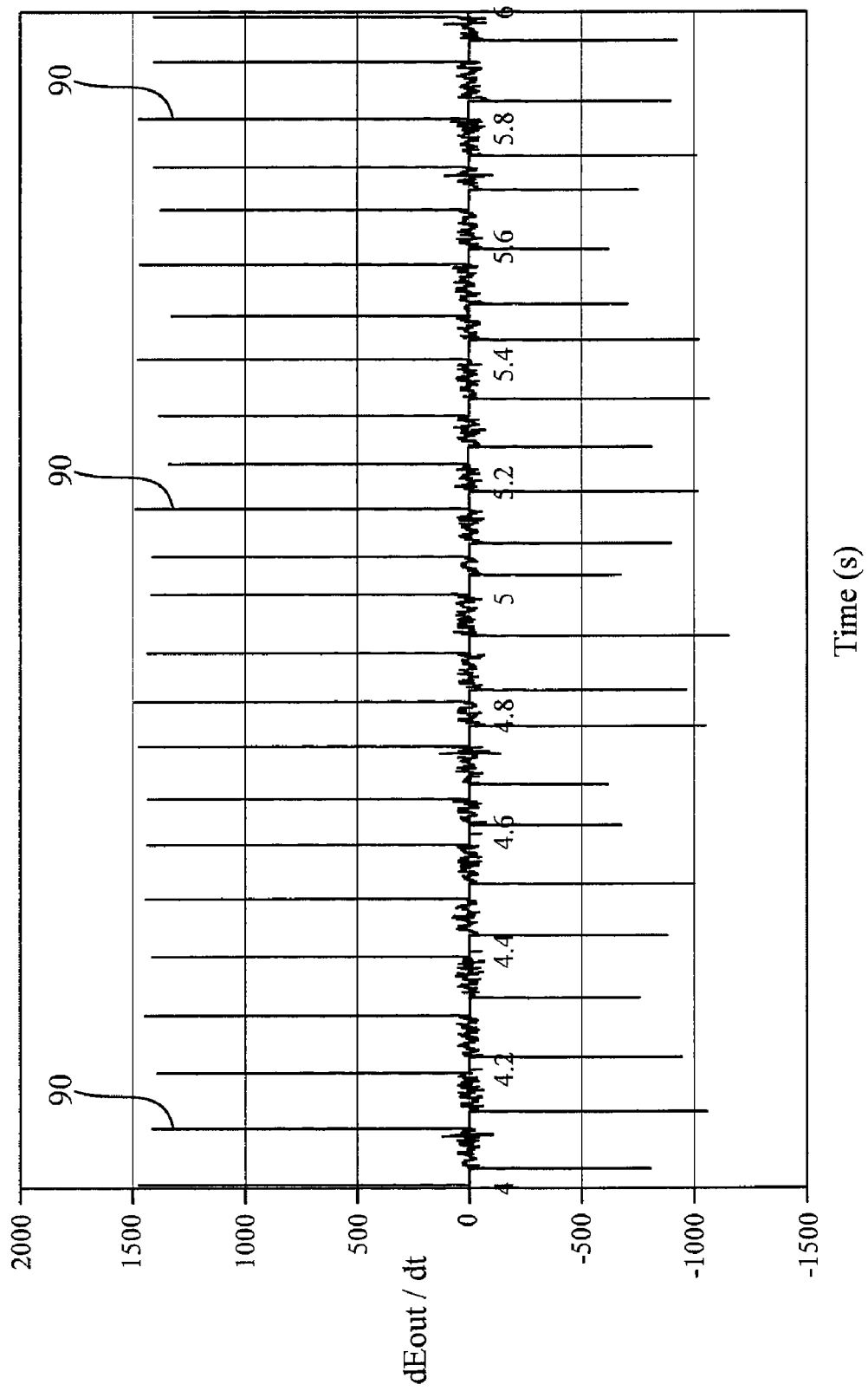
FIG. 3D is a graph displaying the time derivative of the graph in FIG. 3C.

Referring now to FIG. 3C, a voltage signal pattern is shown from a fast drip (about 12 drips/second) through an embodiment of the IV administration set 10 as shown in FIG. 1. In FIG. 3C, $V_{out}$ was again sampled at about 1000 Hz. Again, each of the broader peaks 102 is actually comprised of many data points; thus a simple voltage threshold trigger is inadequate to provide a clean signal. Therefore a clean signal, as seen in FIG. 3D, is provided again by using a slope triggering algorithm. Here a slope trigger of about 1250 V/s is used to produce a single trigger event 90 per drip which is completely adequate for use with a drip counting device.

Although the IV administration set 10 embodiment shown in FIG. 1 produces a very clean signal, it has a few drawbacks that are remedied by other embodiments. For example, the hanging configuration of the first and second leads 40 and 42 may be undesirable in some situations. For example, in some embodiments the hanging first and second leads 40 and 42 require exacting alignment of the output 24 and the contact portions 44 of the leads 40 and 42. This alignment ensures that the droplets 18 adequately contact the leads 40 and 42 to permit accurate counting of the drops 18. Thus, the embodiment of FIG. 1 may not be favorable for environments non-conducive to stabile conditions.

Figure 4:
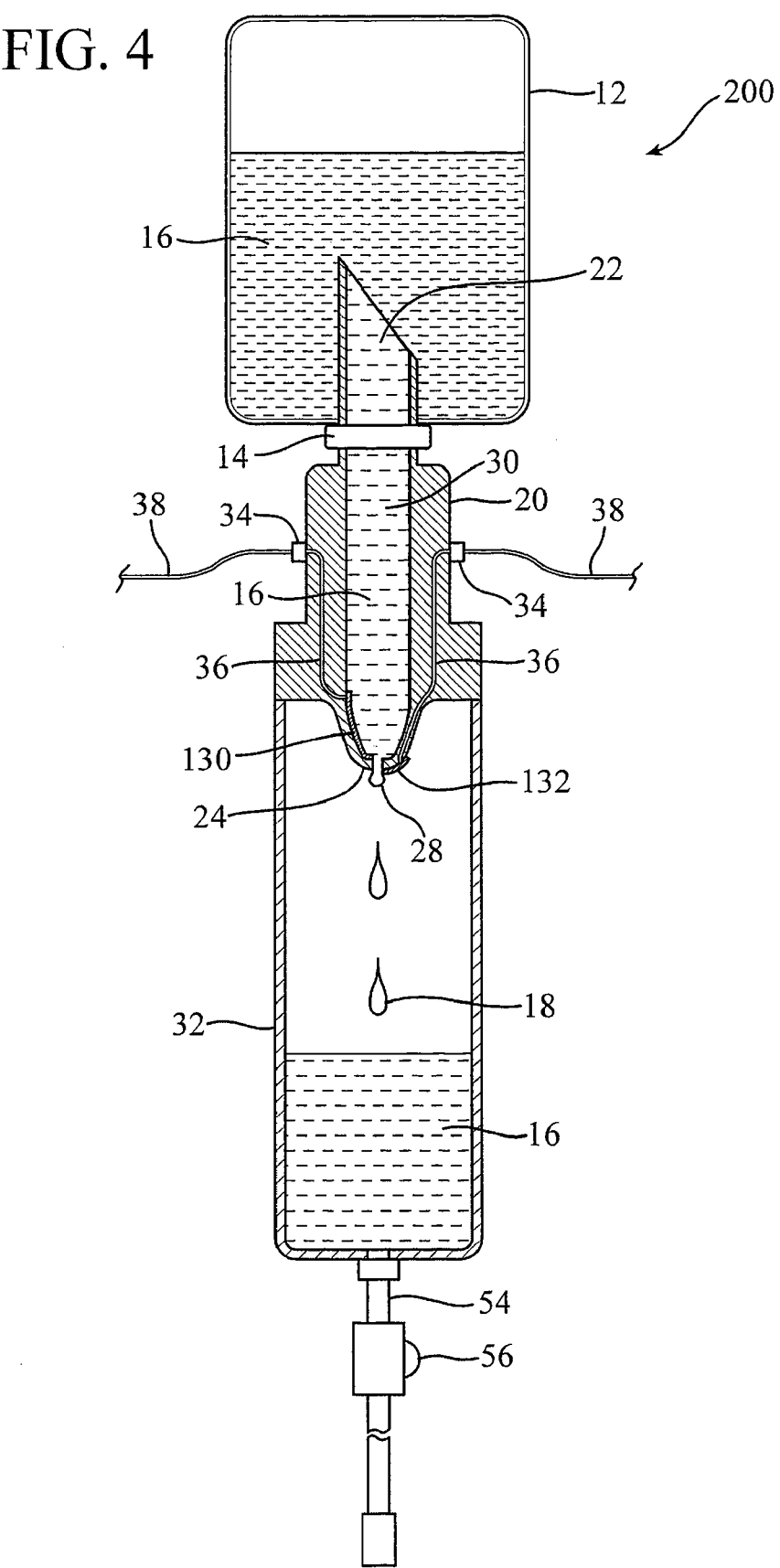
FIG. 4 is a cross-sectioned view of an implementation of an IV administration set comprising a central lead and an external lead.
Figure 5:
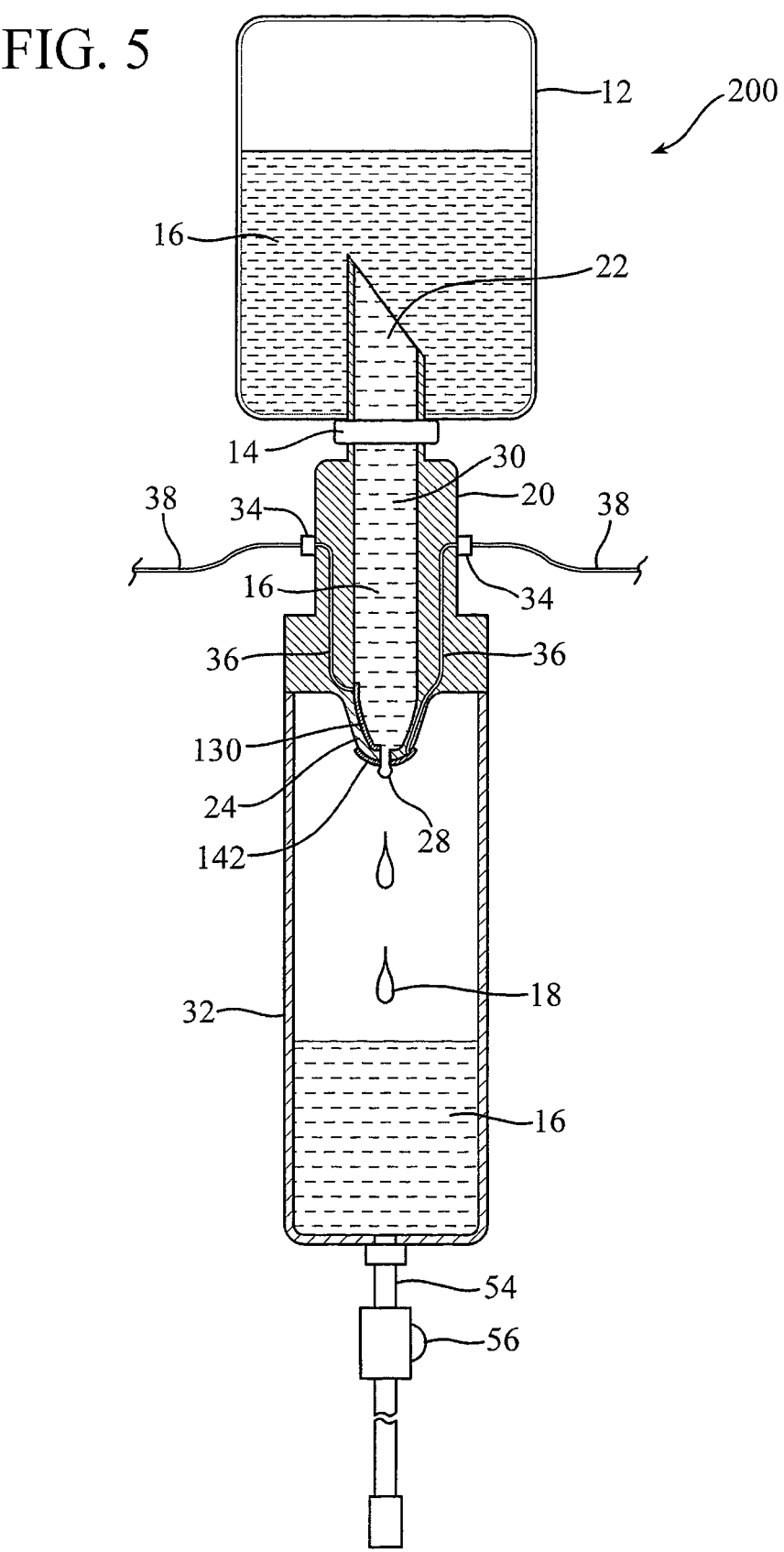
FIG. 5 is a cross-sectioned view of an implementation of an IV administration set comprising an annular external lead.
Figure 6:
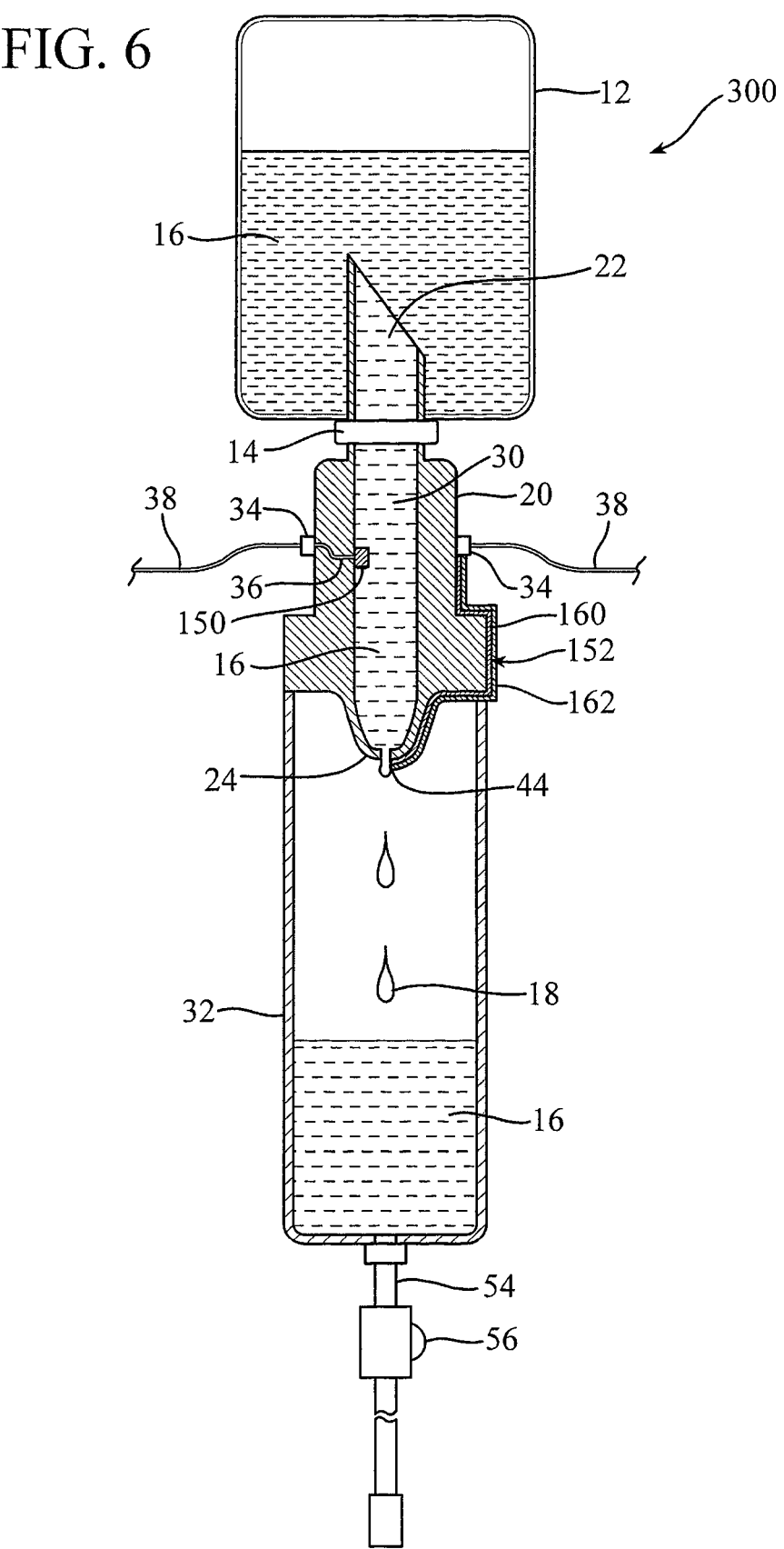
FIG. 6 is a cross-sectioned view of an implementation of an IV administration set comprising an external lead and a central lead.

In some embodiments, the coupling assembly 20 is modified to include a central lead 130 that is located within the fluid channel 30, such that the central lead 130 is always in contact with the fluid 16, as shown in FIGS. 4-6. Referring now to FIG. 4, in some embodiments, the central lead 130 is applied to a surface of the fluid channel 30 so as to be in contact with a fluid 16 within the fluid channel 30. These embodiments further comprise an external lead 132 that is placed on an outer surface of the coupling assembly 20 proximate to the output 24 of the fluid channel 30. Thus, the central lead 130 and the external lead 132 act as a virtual switch that is closed when a drop of fluid 28 contacts the external lead 132. For example, when the drip 28 grows to sufficient size, the drip 28 contacts the external lead 132 and closes the circuit 60 (not shown). When the drip 18 leaves the fluid channel and no longer contacts the external lead 132, the circuit is reopened resulting in a measurable trigger event.

Various methods and configurations may be used to achieve drip monitoring according to the present invention. For example, referring now to FIG. 5 an embodiment incorporating a central lead 130 and an external lead 142 is shown. In this embodiment, the external lead 142 is annularly configured to circumscribe the outlet 24 of the fluid channel 30. As such, the surface area of the external lead 142 is greater than the external lead 132 of the embodiment in FIG. 4. In some embodiments, the increased surface area of the external lead 142 compensates for tilting of the IV administration set 200 that may occur during use. This feature may be useful for situation and circumstances where the spatial stability of the IV set 200 is uncertain.

Referring now to FIG. 6, an embodiment of an IV administration set 300 is shown incorporating a central lead 150 and an external lead 152. In this embodiment, the external lead 152 is a wire 160 that has been applied to the outer surface of the coupling assembly 20. Additionally, a non-conductive coating 162 has been selectively applied to the wire 160 so as to expose only a terminal contact portion 34, and a contact portion 44 of the lead 152. Alternatively, any method of creating a conductive path may be employed including a coated path or a photochemically deposited path. The central lead 150 has also been repositioned closer to the input 22 of the fluid channel 30. Thus, as the fluid reservoir 12 and the fluid channel 30 empty, the fluid 16 within the fluid channel 30 will cease contact with the central lead 150 at a time prior to the complete emptying of the fluid channel 30. Once the fluid 16 and the central lead 150 are no longer in contact, the circuit 60 (not shown) of the system with remain open and the drip counting will cease. In some embodiments, the signaling device 80 (not shown) further includes logic that provides an audible or visual alert when the drip counting stops. This alert informs the user that the fluid channel 30 is nearly empty thereby allowing the user to stop the fluid flow prior to running the IV set 300 dry. In other embodiments, the position of the central lead 150 relative to the contact portion 44 of the external lead 152 is adjusted to increase or decrease the resistance of the fluid 16 between the two leads 150 and 152.

Figure 7:
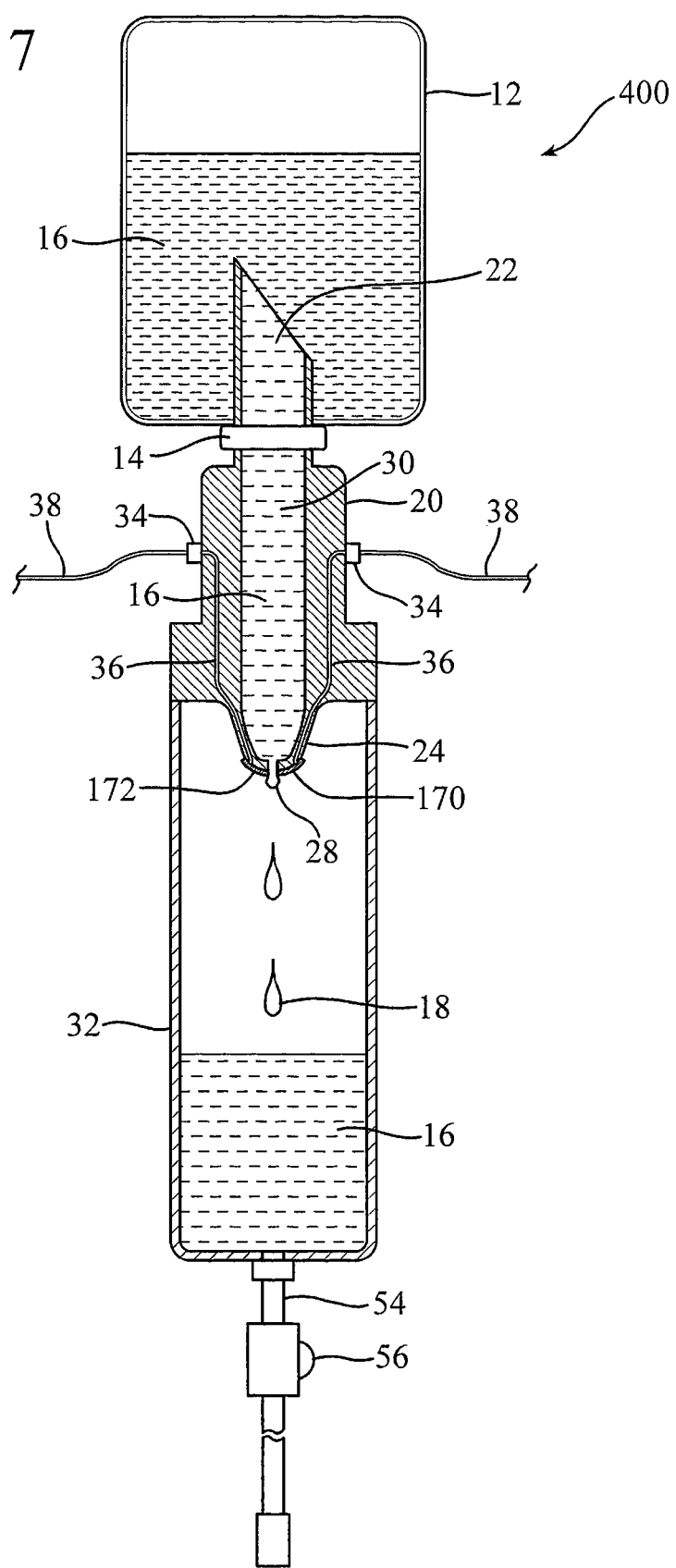
FIG. 7 is a cross-sectioned view of an implementation of an IV administration set comprising multiple external leads.

Referring now to FIG. 7, an additional embodiment of an IV administration set 400 is shown incorporating dual external leads 170 and 172. In this embodiment, the external leads 170 and 172 comprise an electrically-conductive material that has been applied to a surface of the coupling assembly 20 proximate to the output 24 of the fluid channel 30. The coupling assembly 20 further comprises a pair of embedded lead wires 36 connecting the external leads 170 and 172 to the terminal contacts 34. Therefore, the fluid 16 emerged from the fluid chamber 30 and contacts the external leads 170 and 172, thereby closing the circuit 60 (not shown) to provide a measurable trigger event.

Figure 8:
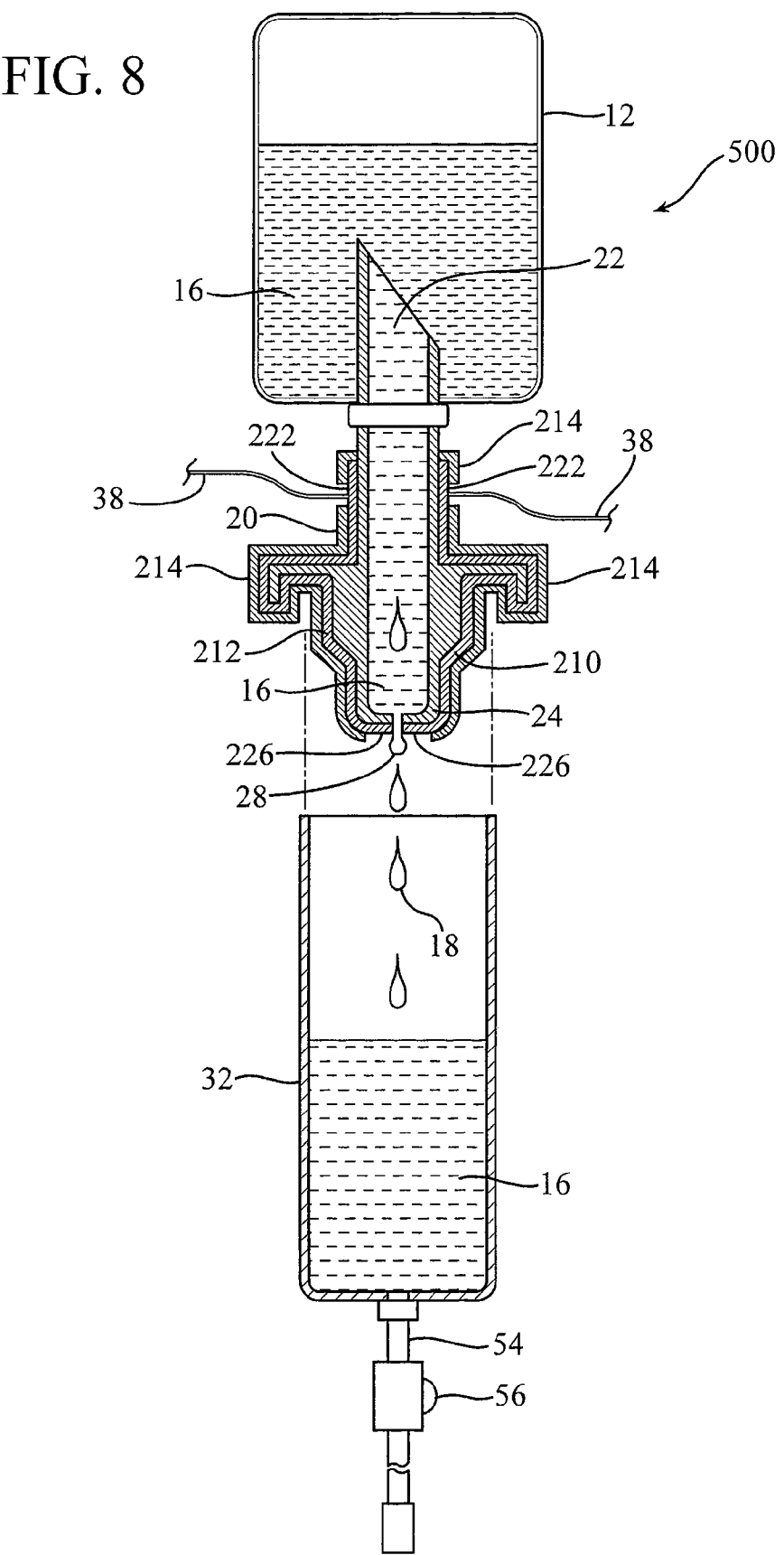
FIG. 8 is an exploded, cross-sectioned view of an implementation of an IV administration set comprising external leads having insulated portions.

Referring now to FIG. 8, an exploded, cross-sectioned view of an implementation of an IV administration set 500 is shown. In this embodiment, the first and second leads 210 and 212 of the IV set 500 are positioned on an external surface of the coupling assembly 20. In accordance with the present invention, the leads 210 and 212 are comprised of any electrically conductive material, such as a metallic material including wire, foil, mesh, and tape. In some embodiments, the leads 210 and 212 comprise an electrically conductive coating material, such as a polymer, an epoxy, a paint, a grease, a sealant, an elastomer, and a carbon coating, that is applied directly to the outer surface of the coupling assembly 220. In some embodiments, portions of the leads 210 and 212 are further coated with a non-conductive protective coating 214. The protective coating 214 is provided as an insulating layer to limit accessibility to desired portions of the leads 210 and 212. For example, in some embodiments a protective coating 214 is applied to the leads 210 and 212, leaving access only to terminal contact portions 222 and contact portions 226 of the respective leads 210 and 212. Again, the contact portions 226 act as a virtual switch that is closed by the presence of an engaged drop 28. In some embodiments, the terminal contacts 222 are accessed via an external drip signaling device to record or indicate flow through the IV set 500.

It should be noted that for all of the embodiments in accordance with the present invention, the terminal contacts 34 are hermetically sealed such that electrical contact can be made with the leads inside the drip chamber 32, without disturbing the flow of the fluid 16 though the IV administration sets 10, 200, 300, 400 and 500. It should also be noted that the interface between the coupling assembly 20 and the drip chamber 32 is also hermetically sealed to prevent disturbance of the fluid flow through the IV administration sets.

Figure 9:
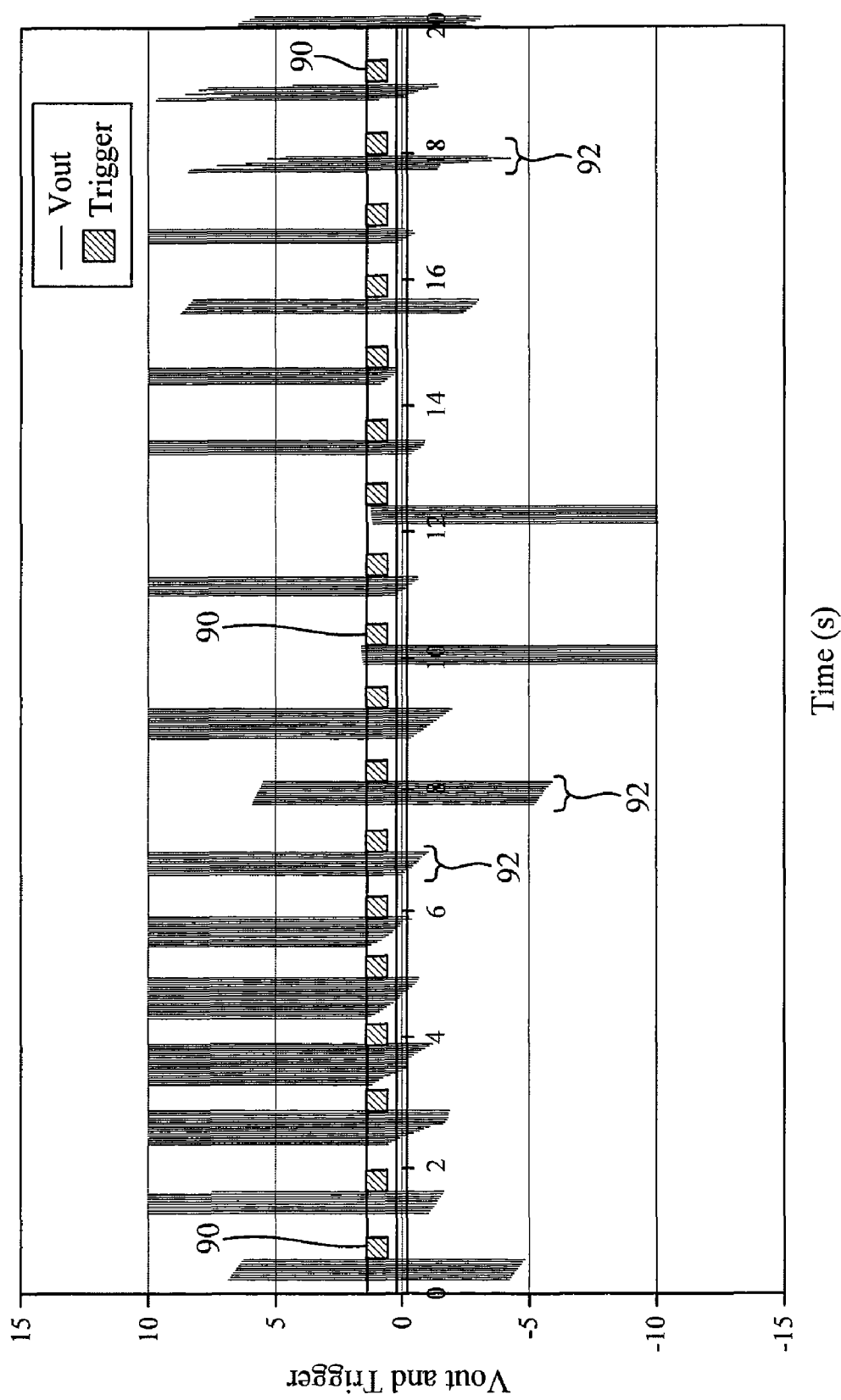
FIG. 9 is a graph displaying results from a drip through an IV administration set having a central lead.

While the embodiments shown in FIGS. 4-8 are less sensitive to alignment issues, these embodiments do not produce a clean signal as does the embodiment of FIG. 1. Referring now to FIG. 9, a graph is shown displaying the $V_{out}$ signal and noise obtained an IV administration set incorporating a central lead in accordance with the present invention. As shown, when a drip is present a resultant broad-band noisy current flows in the circuit. However, when the drip is not present, no current flows thereby allowing drip detection. Thus, in this case a running variance of the past five data samples was calculated, and a negative slope trigger applied to the variance signal. The trace 92 in FIG. 9 shows that the slope trigger on the variance signal produces one, and only one trigger event 90 per drip, as is desirable. Thus, it is evident that much can be done with signal processing to overcome poor or noisy signals, as shown.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

What is claimed is:

1. An intravenous delivery system having an integrated flow monitoring device, the device comprising:
a coupling assembly having an input, an output, and a fluid channel, the input configured for coupling to a fluid reservoir to provide flow of a fluid from the fluid reservoir to the output via the fluid channel, wherein the flow of fluid exits the output as a fluid drop;
an electrical circuit having an output, a power source, an electrical current sensor, a first lead, and a second lead, the power source interposedly connected between the first lead and the second lead, the electrical current sensor interposedly connected between the first lead and the power source, the first lead having a proximal end coupled to a first portion of the coupling assembly and a distal end extending therefrom, and the second lead having a proximal end coupled to a second portion of the coupling assembly and a distal end extending therefrom, wherein the distal ends of the first and second leads are positioned in the pathway of the fluid drop, and wherein simultaneous contact between the fluid drop and the distal ends of the first and second leads completes the electrical circuit; and
a signaling device coupled to the output of the electrical circuit to provide a signal upon completion of the electrical circuit.

2. The device of claim 1, further comprising a drip chamber having an input, an output, and a second fluid reservoir, the input of the drip chamber being coupled to the output of the coupling assembly, the distal ends of the first and second leads being positioned at a height greater than the second fluid reservoir, and the output of the drip chamber being positioned at a bottom portion of the second fluid reservoir, wherein a plurality of fluid drops from the fluid reservoir is collected in the second fluid reservoir, and exits the drip chamber via the output of the drip chamber.

3. The device of claim 1, wherein a portion of the first lead is positioned within the fluid channel, and a portion of the second lead is positioned external to the fluid channel.

4. The device of claim 1, further comprising a first lead wire interconnecting the proximal end of the first lead and the electrical current sensor, and a second lead wire interconnecting the proximal end of the second lead and the power source.

5. The device of claim 1, wherein completion of the electrical circuit sends a signal to the signaling device to indicate the fluid drop.

6. The device of claim 1, wherein the signaling device is at least one of a digital display, a light bulb, a speaker, a printer, a screen, and a diode.

7. The device of claim 1, further comprising a first contact and a second contact positioned on an external surface of the coupling assembly, the first contact interposedly positioned between the first lead and the power source, and the second contact interposedly positioned between the second lead and the power source, wherein the first and second contacts couple the signaling device.

8. The device of claim 7, wherein the signaling device further comprises a first terminal and a second terminal to compatibly couple the first and second contacts of the coupling assembly.

9. The device of claim 8, wherein the first and second terminals are cables.

10. A method for manufacturing an intravenous delivery system having an integrated flow monitoring device, the method comprising:
providing a coupling assembly having an input, an output, and a fluid channel, the input being configured to insert within a fluid reservoir to provide flow of a fluid from the fluid reservoir to the output via the fluid channel, wherein the flow of fluid exits the output as a fluid drop;
providing an electrical circuit having an output, a power source, a resistor, a first lead, and a second lead;
coupling a first portion of a proximal end of the first lead to a first portion of the coupling assembly, and coupling a second portion of the proximal end of the first lead to the power source;
coupling a first portion of a proximal end of the second lead to a second portion of the coupling assembly, and coupling a second portion of the proximal end of the second lead to the power source;
interposing the electrical current sensor between the first lead and the power source;
positioning the distal end of the first lead, and a distal end of the second lead in a pathway of the fluid drop, wherein simultaneous contact between the fluid drop and the distal ends of the first and second leads completes the electrical circuit;
providing a signaling device coupled to the output of the electrical circuit to display a signal upon completion of the electrical circuit.

11. The method of claim 10, further comprising providing a drip chamber having an input, an output and a second fluid reservoir, the input of the drip chamber being coupled to the output of the coupling assembly, the distal ends of the first and second leads being positioned at a height greater than the second fluid reservoir, and the output of the drip chamber being positioned at a bottom portion of the second fluid reservoir, wherein a plurality of fluid drops from the fluid reservoir is collected in the second fluid reservoir, and exits the drip chamber via the output of the drip chamber.

12. The method of claim 10, further comprising positioning a portion of the first lead within the fluid channel, and positioning a portion of the second lead external to the fluid channel.

13. The method of claim 10, further comprising applying a non-conductive material over a portion of the first or second leads to prevent contact between the fluid and the respective lead.

14. The method of claim 10, further comprising providing a first contact and a second contact on an external surface of the coupling assembly, the first contact interposedly positioned between the first lead and the power source, and the second contact interposedly positioned between the second lead and the power source, wherein the first and second contacts couple the signaling device.

15. The method of claim 14, further comprising providing a first terminal and a second terminal to a surface of the signaling device that forms an interface with the coupling assembly, wherein the first and second terminals compatibly couple the first and second contacts of the coupling assembly.

16. An apparatus of monitoring the flow of a fluid through an intravenous delivery system, the apparatus comprising:
a conduit having an input and an output, the input being configured to receive a fluid, and the output being configured to form the fluid into droplets and to release the droplets from the conduit;

a drip chamber having an input, an output, and a reservoir, the input of the drip chamber being coupled to the output of the conduit, whereby the released droplets are collected in the reservoir, and are released from the drip chamber via the output of the drip chamber;

a circuit partially integrated into the conduit, the circuit having an output, a power source, a resistor, a first lead, and a second lead, the power source interposedly connected between the first lead and the second lead, the resistor interposedly connected between the first lead and the power source, the first lead having a proximal end coupled to a first portion of the conduit and the second lead having a proximal end coupled to a second portion of the conduit, wherein distal portions of the first and second leads are positioned in the pathway of the droplets such that simultaneous contact between the droplets and the distal portions of the first and second leads completes the circuit; and a signaling device removably coupled to an outer surface of the conduit and electrically coupled to the output of the circuit, whereby the signaling device receives a signal from the circuit upon completion of the circuit.

17. The apparatus of claim 16, wherein the distal portions of the first and second leads are positioned at a height greater than the reservoir of the drip chamber.

18. The apparatus of claim 16, wherein a portion of the first lead is positioned within an interior portion of the conduit, and a portion of the second lead is positioned on an external surface of the conduit.

19. The apparatus of claim 16, wherein the signaling device is removably coupled to the outer surface of the conduit via an adhesive.

20. The apparatus of claim 16, wherein the signaling device is removably coupled to the outer surface of the conduit via a magnetic interface.

* * * * *